(12) United States Patent
Giblin

(10) Patent No.: US 7,455,814 B2
(45) Date of Patent: Nov. 25, 2008

(54) METERED DISPENSER AND ASPIRATOR DEVICE

(76) Inventor: Leonard J. Giblin, 101 Christopher Columbus Blvd., Galveston, TX (US) 77550

( * ) Notice: Subject to any disclaimer, the term of this patent is extended or adjusted under 35 U.S.C. 154(b) by 1002 days.

(21) Appl. No.: 10/831,083

(22) Filed: Apr. 23, 2004

(65) Prior Publication Data

US 2005/0238543 A1  Oct. 27, 2005

(51) Int. Cl.
*B01L 3/02* (2006.01)
*B67D 5/08* (2006.01)

(52) U.S. Cl. .......................... 422/100; 422/63; 422/64; 422/65; 422/66; 422/67; 422/68.1; 422/116; 73/863.32; 73/864.01; 73/864.11; 73/864.14; 222/638

(58) Field of Classification Search ................ 422/100, 422/63–67, 68.1, 105, 116; 73/863.32, 864, 73/864.11, 864.14, 864.01; 222/638
See application file for complete search history.

(56) References Cited

U.S. PATENT DOCUMENTS

| 4,478,094 A | * | 10/1984 | Salomaa et al. ........... 73/863.32 |
| 4,554,839 A | * | 11/1985 | Hewett et al. ............. 73/864.16 |
| 4,586,546 A | * | 5/1986 | Mezei et al. .................... 141/2 |
| 4,680,266 A | | 7/1987 | Tschopp et al. |
| 5,104,621 A | * | 4/1992 | Pfost et al. ..................... 422/67 |
| 5,424,209 A | | 6/1995 | Kearney |
| 5,707,868 A | | 1/1998 | Boulay et al. |
| 5,759,847 A | | 6/1998 | Eden et al. |
| 6,022,742 A | | 2/2000 | Kopf |
| 6,063,339 A | * | 5/2000 | Tisone et al. ................... 422/67 |
| 6,066,497 A | | 5/2000 | Powell |
| 6,096,532 A | | 8/2000 | Armstrong et al. |
| RE38,281 E | * | 10/2003 | Tisone ........................ 422/100 |
| 6,694,197 B1 | * | 2/2004 | Hatcher et al. ................ 700/56 |
| 6,787,111 B2 | * | 9/2004 | Roach et al. ................... 422/99 |
| 6,868,875 B2 | * | 3/2005 | De Beukeleer et al. ....... 141/130 |
| 7,025,933 B2 | * | 4/2006 | Ganz et al. ..................... 422/63 |
| 7,105,132 B2 | * | 9/2006 | Shumate et al. ............. 422/100 |
| 7,159,740 B2 | * | 1/2007 | Nanthakumar et al. ...... 221/224 |
| 2001/0008615 A1 | * | 7/2001 | Little et al. .................. 422/102 |
| 2002/0012611 A1 | * | 1/2002 | Stylli et al. ................... 422/65 |
| 2002/0104389 A1 | * | 8/2002 | Hovey ...................... 73/864.17 |
| 2002/0159919 A1 | * | 10/2002 | Churchill et al. ............ 422/100 |
| 2002/0168297 A1 | * | 11/2002 | Shvets et al. ................ 422/100 |
| 2002/0176803 A1 | * | 11/2002 | Hamel et al. ................ 422/100 |
| 2003/0113233 A1 | * | 6/2003 | Nanthakumar .............. 422/100 |
| 2003/0215957 A1 | * | 11/2003 | Lemmo et al. .............. 436/180 |

(Continued)

*Primary Examiner*—Brian R. Gordon
(74) *Attorney, Agent, or Firm*—Sherman D. Pernia; Karen A. Rex

(57) ABSTRACT

An automated metered fluid dispensing and aspirating apparatus comprising a combination delivery/removal fluid head with upper shuttle and lower reservoir assemblies is disclosed. A covered, variably positionable well table allows for mounting sample wells and automatically presenting at least one array of sample or reaction wells to the delivery/removal fluid head at a time. A fluid handling system of inter-connected tubing, pumps and valves interfaces with the delivery/removal fluid head. The fluid handling system provides reagents to and removes waste from the delivery/removal fluid head and sample wells. A control assembly, including a central processing unit and hardware, software and gas pressure sources, provides for time responsive operation and control of the delivery/removal fluid head, drive mechanisms for the table and fluid head, fluid handling system and well table. The entire apparatus is mounted on its own platform and includes separate housings for control and sample handling sections.

21 Claims, 7 Drawing Sheets

U.S. PATENT DOCUMENTS

| | | | |
|---|---|---|---|
| 2004/0022689 A1* | 2/2004 | Wulf et al. | 422/100 |
| 2004/0033554 A1* | 2/2004 | Powers | 435/29 |
| 2004/0096360 A1* | 5/2004 | Toi et al. | 422/63 |
| 2005/0130318 A1* | 6/2005 | Vann et al. | 436/180 |
| 2005/0232822 A1* | 10/2005 | Reed et al. | 422/100 |
| 2007/0014694 A1* | 1/2007 | Beard et al. | 422/100 |

* cited by examiner

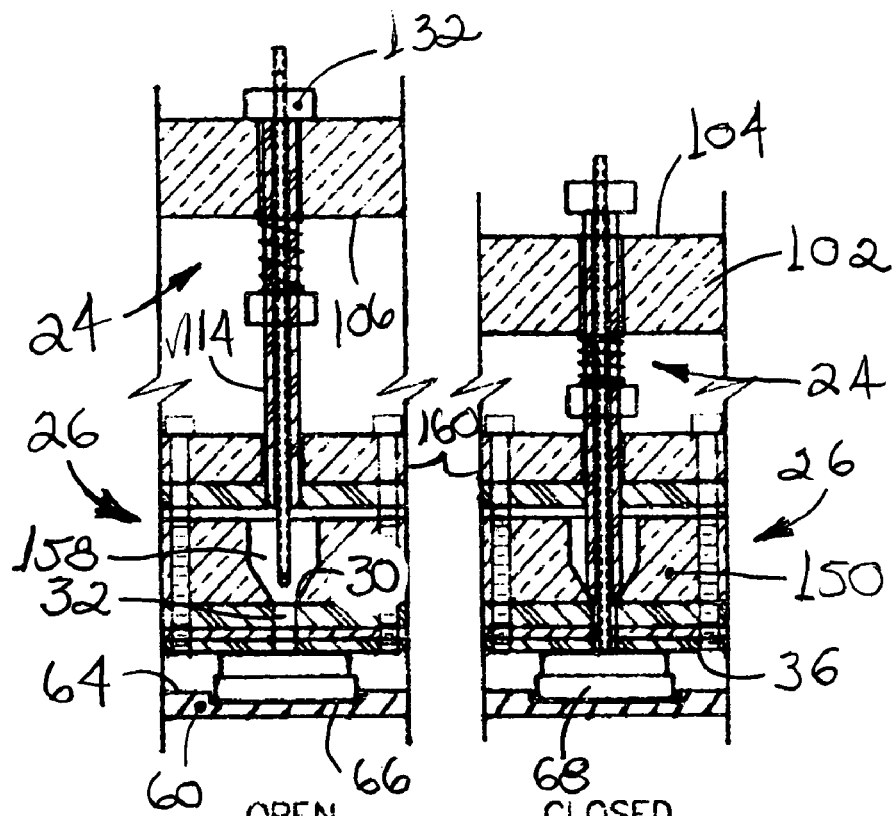
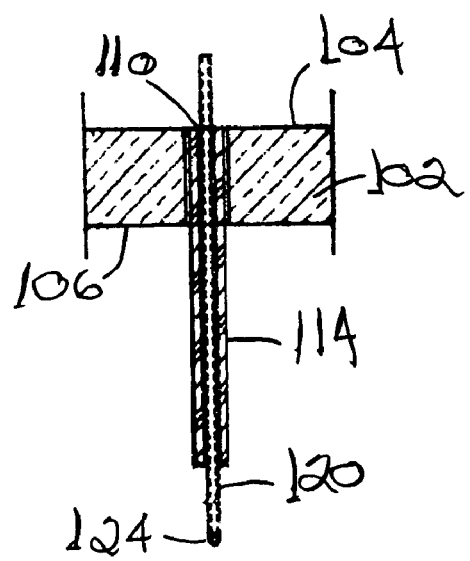

OPEN      CLOSED

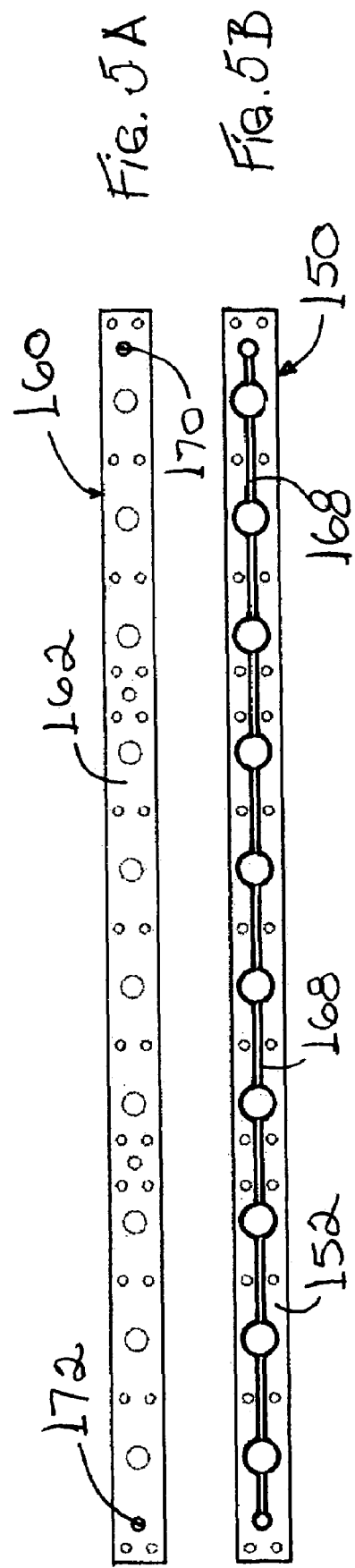

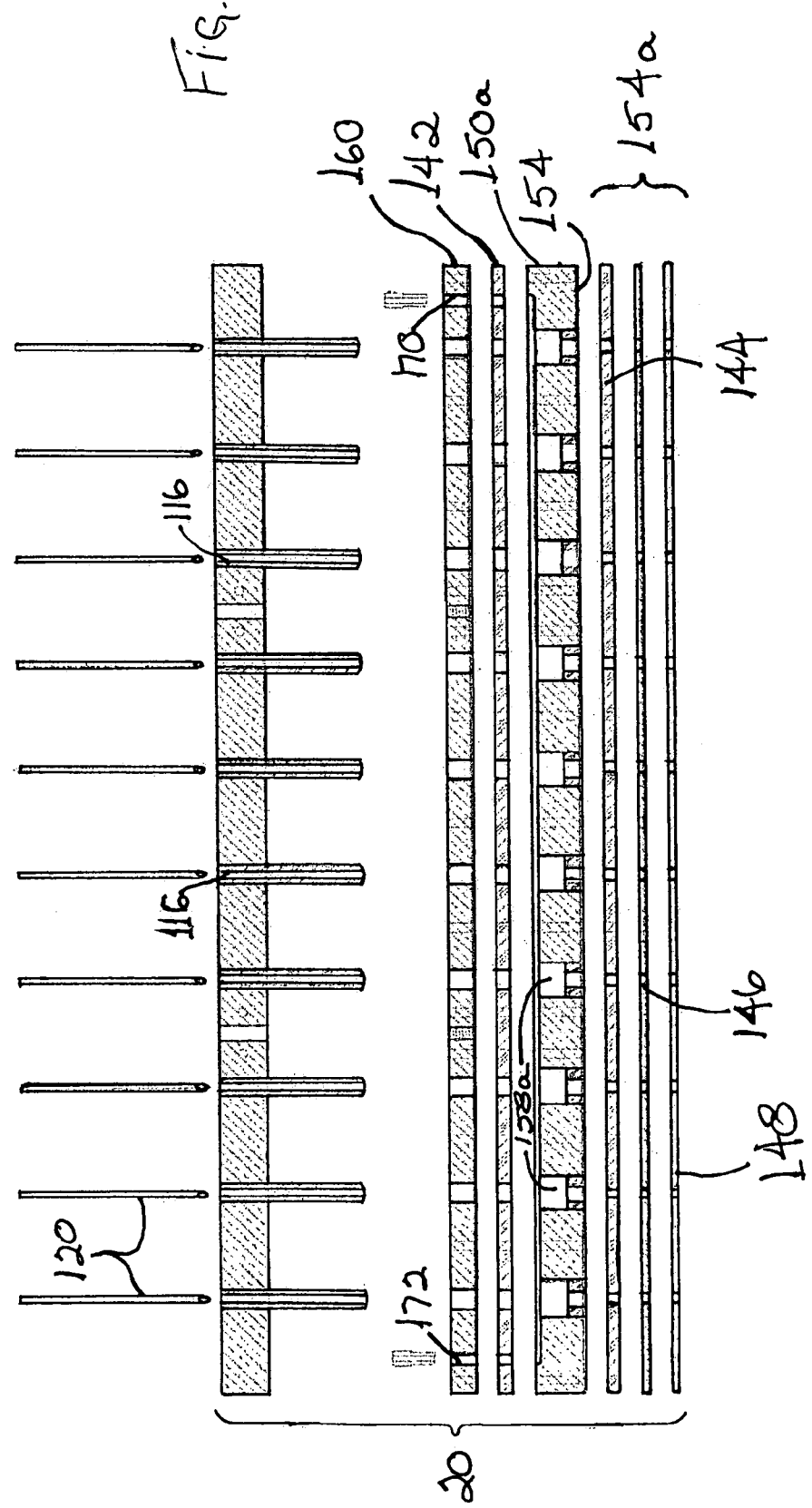

METERED DISPENSER AND ASPIRATOR DEVICE

FIELD OF THE INVENTION

The present invention is in the field of chemistry, biochemistry and microbiology. More specifically, the present invention relates to an automated apparatus having means to lyse or rupture cells on a slide for microscopic examination by addition of a material. Further, the apparatus comprises time responsive means to control the positioning of movable components, including a covered (environmentally sealed), multiple well tray and a liquid material (fluids) dispensing and handling means. In particular, the present application relates to the fluid dispensing component of the apparatus.

SUMMARY OF THE INVENTION

The present invention is an apparatus useful in the fields of tissue culture and cytogenetics for the automated delivery and removal of fluids from a plurality of sample wells. More specifically, the present invention is an automated metered fluid dispensing and fluid aspirating apparatus. The present invention comprises a combination delivery/removal fluid head separable into an upper shuttle assembly and a lower reservoir assembly, with the shuttle assembly being variably positionable relative to the reservoir assembly by a drive mechanism. A covered, variably positionable well table provides a mechanism for mounting the sample wells and for automatically presenting at least one array of sample or reaction wells to the combination delivery/removal fluid head at a time. The well table cover closely covers each sample well and substantially reduces any evaporation of liquids from the sample wells during operation of the apparatus. Additionally, a fluid handling system of inter-connected tubing, pumps and valves in flow communication with reagent sources and waste reservoirs interfaces with the combination delivery/removal fluid head. The fluid handling system provides reagents to and removes waste from the combination delivery/removal fluid head and the sample wells. A control assembly, including a central processing unit and appropriate hardware, software and gas pressure sources, provides for the time responsive operation and control of the combination delivery/removal fluid head, the drive mechanisms for the table and the fluid head, the fluid handling system and the well table. The entire apparatus is mounted on its own platform and includes separate housings for control and sample handling sections.

In particular, the present invention relates to the delivery/removal fluid head of the present invention. The delivery/removal fluid head is a combination of an upper shuffle assembly and a lower reservoir assembly. The shuttle assembly is variably positionable relative to the reservoir assembly by a separate fluid head drive mechanism. The delivery/removal fluid head assembly includes an array of decanting ports each in fluid/gas communication with a metered fluid reservoir. A fluid charging manifold, in fluid/gas communication with each metered reservoir, moves fluids materials (including reagent solutions) and gases into and out of the fluid head to charge the fluid reservoirs. The opening and closing of the decanter ports at the bottom of each fluid reservoir is accomplished by the seating and unseating of a shuttle peg against the decanter port at the bottom of the reservoir. The shuttle pegs are fixed to the shuttle assembly of the fluid head and are seated against decanter ports or removed from the fluid reservoirs by operation of the head drive mechanism positioning the shuttle assembly relative to the reservoir assembly.

The shuttle pegs are hollow tubes. An aspirator nozzle is inserted into and freely passes through the hollow of each shuttle peg. When a shuttle peg is seated against its corresponding decanter port, the lower end of the peg's aspirator nozzle extends through the shuttle peg and into a sample well positioned below the decanter port of the fluid head. The upper end of the aspirator nozzle is in controlled communication with a low vacuum pressure source. With the shuttle assembly in this position (shuttle pegs seated in the decanter ports), fluids in the sample well may be aspirated from the sample well or dish. Additionally, with the shuttle assembly in this position, the fluid reservoirs of the reservoir assembly may be filled. In fact, the fluid reservoirs may be charging with a liquid reagent while the sample wells are being aspirated. The reagent solution is delivered from the fluid reservoirs into the wells below the fluid head by moving the shuttle assembly away from the reservoir assembly, which unseats the shuttle pegs from the decanter ports and withdraws them from the fluid reservoirs.

BRIEF DESCRIPTION OF THE DRAWINGS

FIG. 2A is a partial cross-sectional view of a front elevation of the fluid delivery and removal head ("fluid head") shown in an "open" configuration, and illustrating the close positioning of a sample well to the bottom or decant surface of the fluid head.

FIG. 2B is similar to FIG. 2A, but showing the fluid delivery and removal head ("fluid head") in an "closed" configuration, where the shuttle assembly has been driven downward to seat its shuffle pegs in the decanter ports.

FIG. 2C illustrates aspirator tubes biased in proper relationship to the shuttle pegs by gravity.

FIG. 5A is a bottom plan view of the sealing surface of the manifold cover of a reservoir assembly of the present invention.

FIG. 5B is a top plan view of the manifold block of a reservoir assembly of the present invention.

FIG. 6A is an exploded view of a cross-section through the front plan of a fluid delivery/removal head of the present invention.

DETAILED DESCRIPTION OF THE INVENTION

Figure 1:
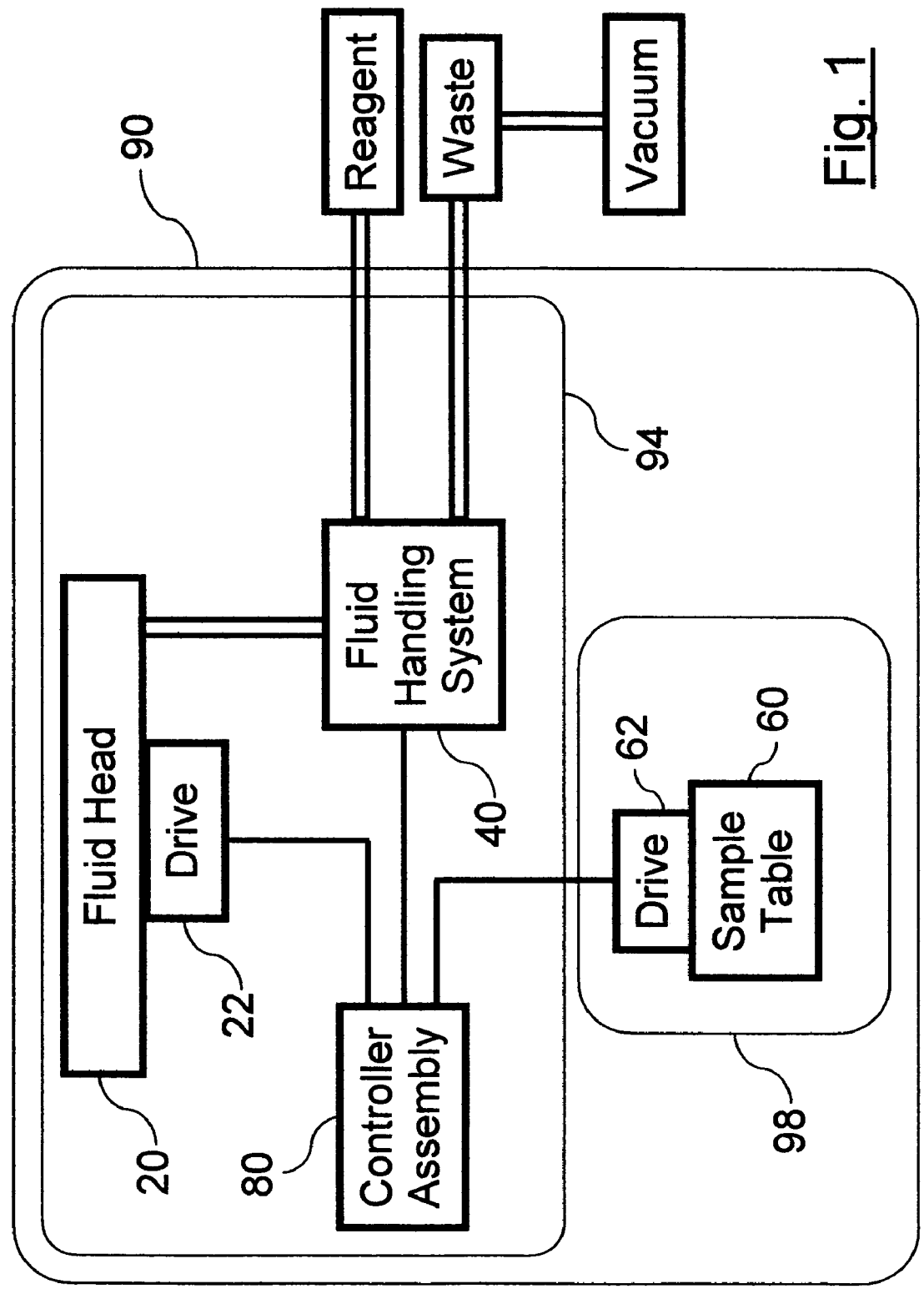
FIG. 1 is a schematic block diagram of the present metered fluid dispensing and aspirating apparatus of the present invention.

Referring now to the drawings, the details of preferred embodiments of the present invention are graphically and schematically illustrated. Like elements in the drawings are represented by like numbers, and any similar elements are represented by like numbers with a different lower case letter suffix.

As illustrated in FIG. 1, the present invention is a metered fluid dispenser and aspirating apparatus comprising a variably positionable well table 60, a fluid delivery/removal head 20, a fluid handling system 40 in flow communication with the fluid head 20 and with source and waste reservoirs (see FIG. 1), and a controller assembly 80 providing for the timed responsive operation and control of the delivery/removal fluid head 20, the fluid handling system 40 and the well table 60.

The sample well table 60 is variably positionable relative to the apparatus platform 90 of the present invention by means of a table drive mechanism 62. The sample table 60 preferably has a plurality of sample well holders 66 arrayed on its surface 64. Each holder 66 provides for mounting one of more sample wells (or dishes) 68. The fluid delivery/removal head 20 is fixed relative to the platform 90. As shown in FIGS. 2A and 2B, the fluid head 20 is disposed closely above the well table 60 such that a sample well or dish 68 disposed on the well table surface 64 contacts the bottom reservoir surface 36 of the fluid head 20 when the sample well 68 is positioned below the fluid head 20. The fluid head 20 provides for the controlled decanting of a metered volume of a liquid material into the sample wells 68 below it, and for removing waste fluids from the sample wells 68. The fluid handling system 40 is in flow communication with the fluid head 20 and with the source (liquid reagent material solutions) reservoirs and with waste reservoirs. The fluid handling system 40 provides for delivering liquid materials to and removing waste from the fluid head 20 under control of the controller assembly 80. The controller assembly 80 includes a central processing unit and appropriate hardware and software (not shown), and is in electrical communication with the well table 60, the fluid head 20 and the fluid handling system 40. The controller assembly 80 provides for the time responsive operation and control of the delivery/removal fluid head 20, the fluid handling system 40 and the well table 60.

The fluid delivery/removal head 20 of the present invention is comprised of two major components: a shuttle assembly 24 and a reservoir assembly 26. See FIG. 2A and FIG. 3. The shuttle assembly 24 is variably positionable relative to the reservoir assembly 26. The reservoir assembly 26 is substantially fixed relative to the platform 90 of the apparatus. The positioning of the shuttle assembly 24 relative to the reservoir assembly 26 is accomplished by means of a head drive mechanism 22 under the control of the controller assembly 80.

The shuttle assembly 24 includes a shuttle bar 102. Preferably, the shuffle 102 bar is a block or a plate made of a material and has dimensions to render it substantially rigid as it is moved or positioned relative to the reservoir assembly 26 by the head drive mechanism 22. In one preferred embodiment, the shuttle bar 102 was made from a plate of an aluminum alloy. However, other materials are selectable by one of ordinary skill in the art for practice as a shuttle bar 102, such as a plastic material, a composite (e.g., carbon-fiber material), and a laminate.

The shuttle bar 102 has an upper bar surface 104 and a lower bar surface 106. A plurality of vertical aspirator ports 110 extending through the shuttle bar 102 between the upper and lower bar surfaces 104 & 106. The aspirator ports 110 are arranged in a dispenser pattern. The dispenser pattern corresponds to the layout of an array of sample well holders 66 on the well table surface 64. At the lower bar surface 106, a shuttle peg 114 extends in a downward direction from each aspirator port 110. In the preferred embodiments of the figures, the shuttle pegs 114 were hollow cylinders with two open peg ends connected via the interior lumen 116 of the shuttle peg 114. In this embodiment the upper open peg end of the shuttle peg 114 defined the aspirator port 110 at the upper bar surface because the shuttle peg 114 passed completely through the shuttle bar 102, and the lumen 116 of the shuttle peg was continuous with the aspirator port 110.

Figures 3A, 3B:
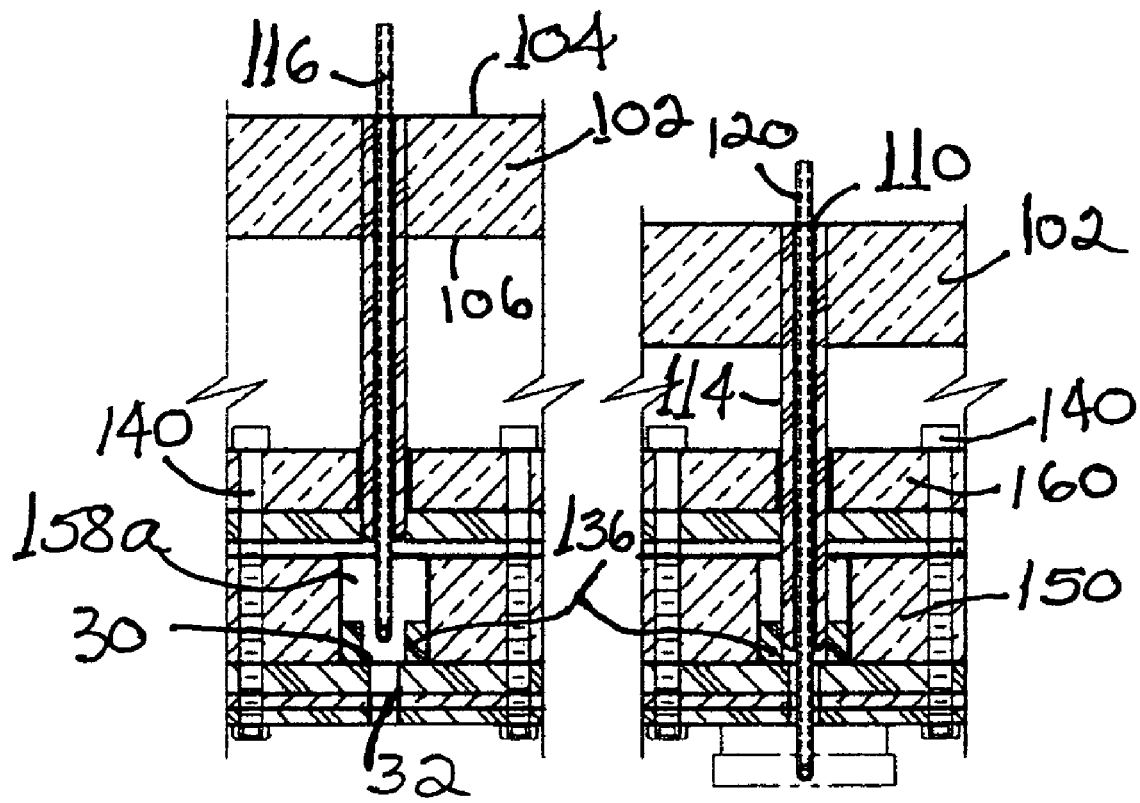
FIGS. 3A and 3B illustrate an alternative configuration of the fluid delivery and removal head shown in FIGS. 2A and 2B, respectively.

FIGS. 3A and 3B illustrate an alternative configuration of the fluid delivery and removal head 20 as practiced in the present apparatus. In this preferred embodiment, the shuttle assembly 24 utilized gravity to bias the aspirator tubes 120 in a downward direction, and did not include the aspirator bias assembly 132 of the embodiment illustrated in FIGS. 2A and 2B. Additionally, FIGS. 3A and 3B illustrate an alternative fluid reservoir 158a. The alternative fluid reservoir 158a had substantially straight cylindrical dimensions, and included a volume insert 136 installed in the bottom of the fluid reservoir 158a. The volume insert 136 was removable and replaceable. This allowed a metered volume of liquid dispensed by the reservoir to be adjustable by selecting the size of the volume insert 136 to reduce the metered volume of the fluid reservoir 158a.

Figure 4:
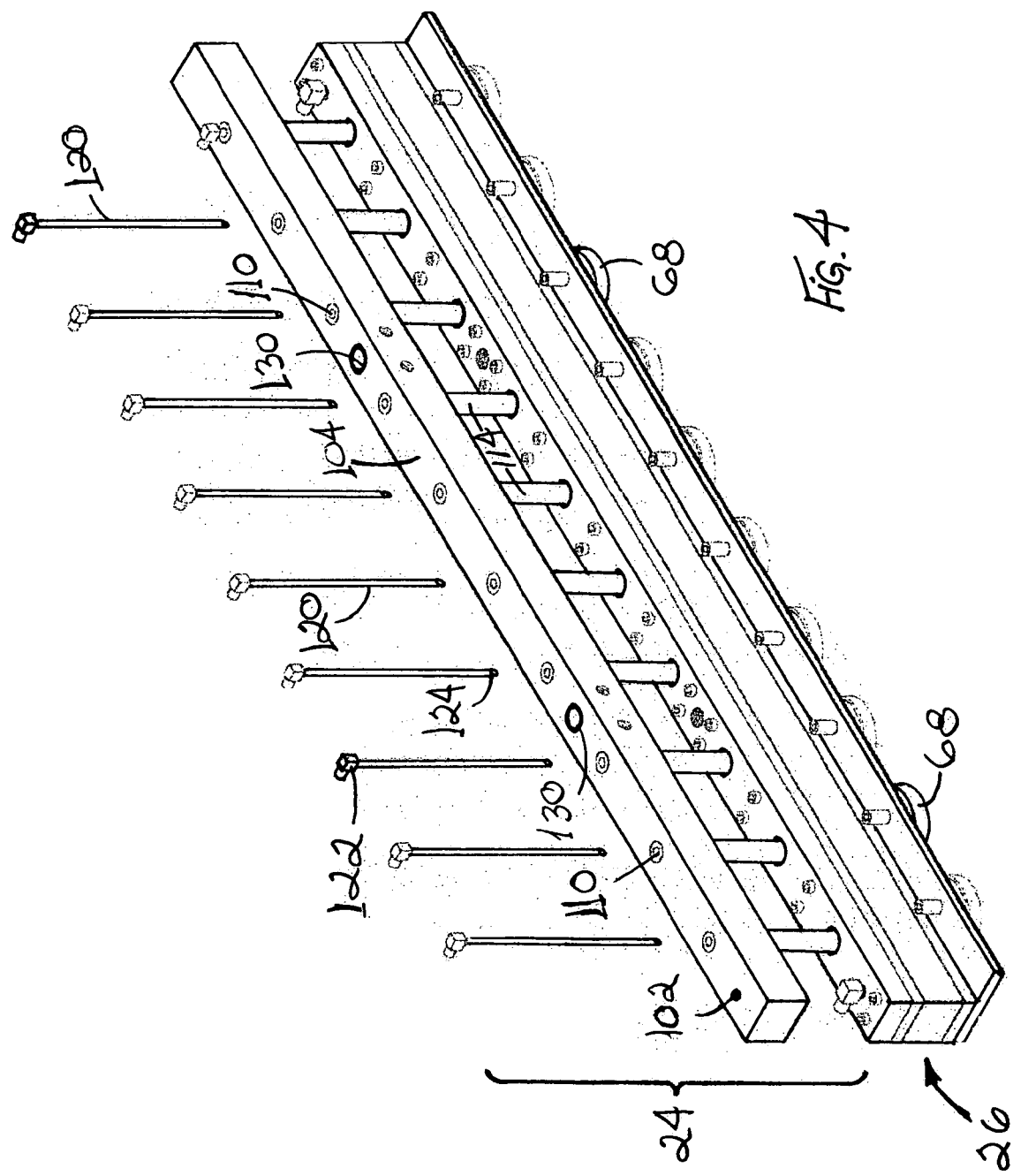
FIG. 4 is a perspective view a fluid head of the present invention showing the relationship of the shuttle assembly to the reservoir assembly.

As illustrated in FIG. 4, the continuous passage defined by the lumen 116 of the shuttle pegs 114 and the aspirator ports 110 each has an aspirator tube 120 loosely received in the continuous passage. The aspirator tube 120 itself is hollow and has a substantially straight portion which inserts into and is slidable within the lumen of the shuttle peg 114. The straight portion of the aspirator tube 120 extends beyond the lower open peg ends of the shuttle peg 114 and above the upper bar surface 104 of the shuttle bar 102. The aspirator tubes have an upper tube end 122 adapted to be connected to a vacuum source and a lower tube end 124 adapted to aspirate a liquid. In the preferred embodiment of the figures, the aspirator tubes 120 were made of stainless steel tubing, and were held in proper relationship in the shuttle pegs 114 by either an aspirator bias assembly 132 (including spring and stops, see FIGS. 2A and 2B) or by gravity (see FIG. 2C).

Preferably, the shuttle pegs 114 are of made a chemically inert material, relative to the liquids with which it comes into contact. In the preferred embodiments shown, the shuttle pegs 114 were screwed into the shuttle bar 102. However, the pegs 114 could have been press-fitted, adhered or fixed to the shuttle bar 102 by any means known to the ordinary skilled artisan. Additionally, it is preferred that the shuttle pegs 114 have a low friction exterior surface. In preferred embodiments of the present apparatus, the shuttle pegs 114 were accomplished in two manners: using polytetrafluoroethylene (TEFLON®) compositions and using molybdenum compositions. However, in view of the teaching herein, other shuttle peg compositions are know to and practicable in the present invention by one of ordinary skill in the art, including other plastic or elastomeric compositions.

In the preferred embodiments shown in the figures, the shuttle bar 102 had at least at least two vertical guide sleeve bores 130 extending through it, between the upper and lower bar surfaces 104 & 106. Drive screw post (not shown) slideably passed through these guide sleeve bores 130, with their lower ends mounted on the reservoir assembly 26. A stepping-drive motor (not shown) was fixed to the shuttle bar 102 and rode up and down the drive screw posts under control of the controller assembly 80. In this manner, the shuttle assembly 24 was positionable relative to the reservoir assembly 26, by the action of the two stepping motors of the fluid head drive mechanism 22. However, other means are known to one of ordinary skill in the art to accomplish the fluid head drive mechanism 22 of the present invention.

As also shown in FIGS. 2A and 2B and others, the reservoir assembly 26 of the fluid delivery/removal head 20 includes a manifold block 150. The manifold block 150 has a substantially flat upper manifold surface 152 and lower manifold surface 154. A plurality of fluid reservoirs 158 extend vertically through the upper and lower manifold surfaces 152 & 154 of the manifold block 150. The fluid reservoirs 158 are disposed in the dispenser pattern. The upper manifold block surface 152 is covered with a manifold cover 160, which is adapted to form a liquid seal against the upper manifold surface 152. The manifold cover 160 has a plurality of peg guide through apertures 164 disposed in the dispenser pattern corresponding to the fluid reservoirs 158. The peg guide apertures 164 each slideably receives and closely-seals against an associated shuttle peg 114 that is inserted through the peg guide apertures 164 and into the corresponding fluid reservoir 158. In the preferred embodiment illustrated in FIGS. 6A and 6B, a manifold gasket head 142 was used to provide a fluid seal for the fluid channel 168.

A fluid channel 168 (see FIG. 5B) disposed between the upper manifold surface 152 and the sealing surface 162 (see FIG. 5A) of the manifold cover 160. The fluid channel 168 communicating with each of the fluid reservoirs 158 and with fluid inlet and outlet ports 170 & 172 in the manifold cover 160. The fluid inlet and outlet ports 170 & 172 are in flow communication with the fluid handling system 40. The manifold cover 160 can be fixedly sealed against the manifold block 150. However, in the embodiment of the figures, the manifold cover 160 was removably sealed against the manifold block 150 using removable fastener 140, e.g., through bolts and nuts or embedded fasteners.

Also, in the embodiment of the figures, the fluid channel 168 was inset into the upper block surface 152 of the manifold block 150, as shown in FIG. 5B. Alternatively, the fluid channel could be inset into the sealing surface 162 of the manifold cover 160. As a further alternative, the fluid channel could be inset into a manifold gasket head 142 (see FIGS. 6A and 6B) disposed between the manifold cover 160 and the manifold block 150. A benefit of the latter is that this feature could be utilized to provide a means of adjusting the volume of the fluid reservoirs 158 or the reach or the shuttle pegs 114 into the fluid reservoirs 158.

The fluid reservoirs 158 of the manifold block 150 have a metered fluid volume defined by the volumetric space of the fluid reservoir 158 minus the volume displacement of the shuttle peg 114, when the shuttle peg 114 is seated in the fluid reservoir 158. In this configuration, the shuttle peg 114 is seated against a peg seat 30 disposed at the bottom of the fluid reservoir 158. The peg seat 30 engages the lower end 118 the associated shuttle peg 114 and seals off the decant passage 32 of the fluid reservoir 158. The open center of the peg seat 30 defines the decant passage 32 of the fluid reservoir 158 at the lower manifold block surface 154. In this manner, the fluid reservoirs 158 of the manifold block 150 have a metered volume for dispensing defined by the volume of the reservoir 158 minus the displacement volume of the shuttle peg 114 when the shuttle peg 114 is seated in the fluid reservoir 158.

In a preferred embodiment practiced in the present invention, the manifold block lower surface 154 was a lower surface laminate 154*a*. The lower surface laminate 154*a* included a bottom gasket 144 adjacent the manifold block lower surface 154, followed by a manifold bottom cover 146 to seal the bottom gasket 144 in place, and a low friction interface 148 (e.g., a polyethylene sheet) below that. The bottom gasket 144 and bottom cover 146 are particularly useful for use with the reservoir block 150*a* of FIGS. 6A and 6B, having fluid reservoirs 158 with volume inserts 136 (see also FIGS. 3A and 3B). The low friction interface 148 allows the sample wells or sample dishes 68 closely engage the bottom surface of the fluid delivery/removal head 20 and freely slide underneath it.

Figure 6B:
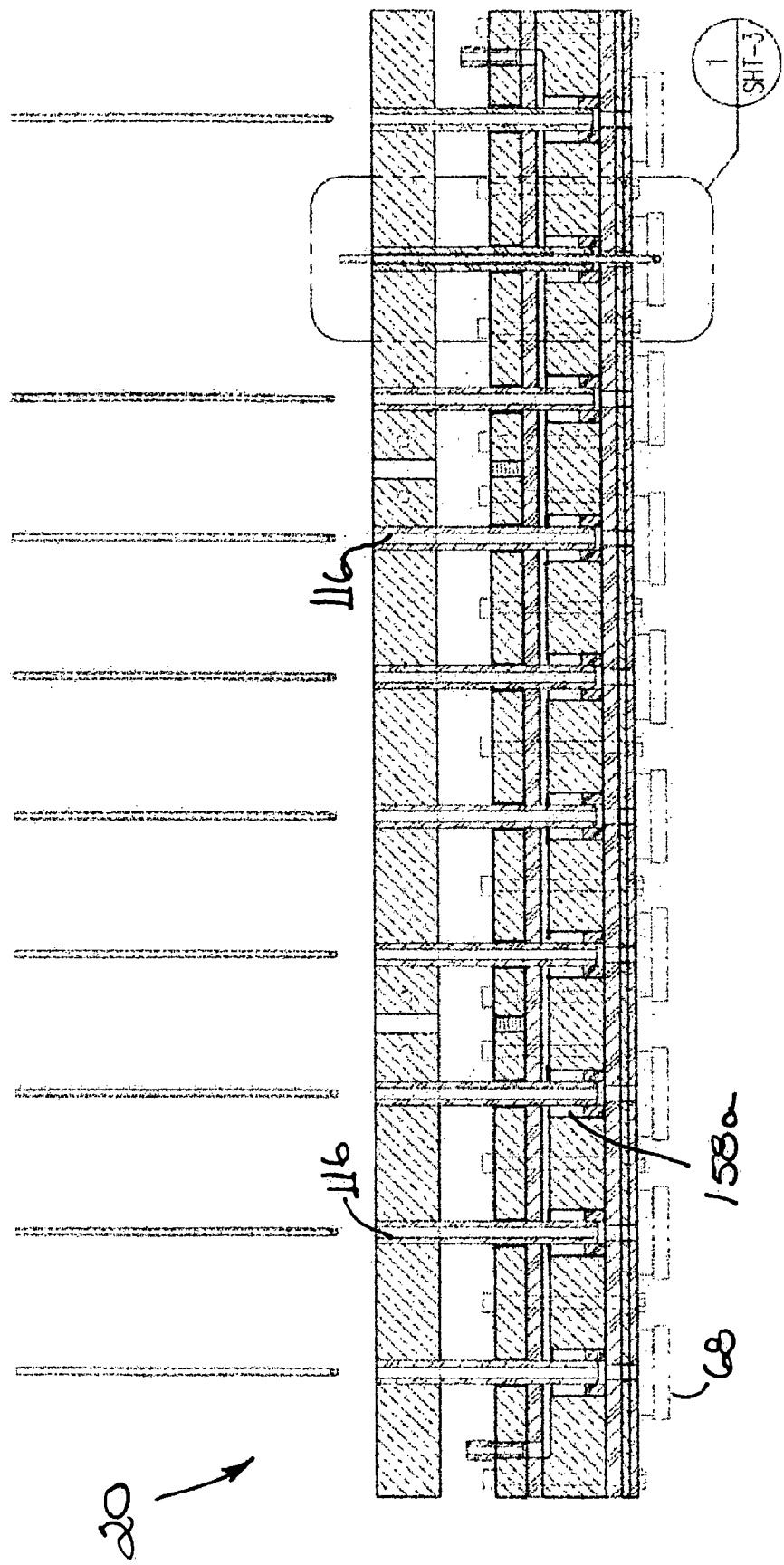
FIG. 6B is a cross-sectional view through the front plan of the assembled fluid delivery/removal head of FIG. 6A.

FIG. 6A is an exploded view of a cross-section through the front plan of a preferred fluid delivery/removal head 20 practiced in the present metered fluid dispenser and aspirating apparatus. The figure shows the combination fluid delivery/removal head 20 comprised a shuttle assembly 24 which was variably positionable relative to the reservoir assembly 26 by a head drive mechanism (not shown). FIG. 6B is a view through the front plan of the fluid delivery/removal head of FIG. 6A in an assembled configuration.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

What is claimed is:

1. A metered fluid dispenser and aspirating apparatus comprising:
   a variably positionable well table disposed on an apparatus platform, the sample table having at least one array of sample wells disposed on its surface, and the table being variably positionable on the platform by means of a table drive mechanism;
   a fluid delivery/removal head, the fluid head comprising a positionable shuttle assembly and a substantially fixed reservoir assembly, the shuttle assembly comprising a shuttle bar having an upper and a lower bar surfaces, and a plurality of vertical aspirator ports extending through the shuttle bar between the upper and lower bar surfaces with the aspirator ports arranged in a dispenser pattern; and a shuttle peg extending in a downward direction from each aspirator port at the lower bar surface, the shuttle peas being tubular and having two open peg ends connected via an interior lumen of the shuttle peg, with the shuttle assembly being variably positionable relative to the reservoir assembly and with the fluid head fixed relative to the platform and disposed closely above the well table such that a sample well disposed on the well table contacts a bottom surface of the fluid head when the sample well is positioned below the fluid head, the fluid head for the controlled decanting a metered volume of a liquid material to the sample wells below it and for removing waste fluids from the sample wells;
   a fluid handling system in flow communication with the fluid head, the fluid handling system for the controlled delivering liquid materials to and removing waste from the fluid head; and
   a controller assembly, including a central processing unit and appropriate hardware and software, the controller assembly in electrical communication with the well table, the fluid head and the fluid handling system, and providing for the time responsive operation and control of the delivery/removal fluid head, the fluid handling system and the well table.

2. The shuttle assembly of claim 1, wherein the shuttle pegs each have an aspirator tube loosely received in the lumen of the shuttle peg, the aspirator tube being hollow and having a substantially straight portion slidable within the lumen of the shuttle peg with the straight portion extendable beyond the open peg ends of the shuttle peg.

3. The shuttle pegs of claim 2, wherein the aspirator tubes have an upper tube end adapted to be connected to a vacuum source and a lower tube end adapted to aspirate a liquid.

4. The shuttle assembly of claim 1, wherein the shuttle bar is comprised of a material and has dimensions to render it substantially rigid as it is variably positioned relative to the reservoir assembly by a drive means.

5. The shuttle assembly of claim 4, wherein the shuttle bar comprises a plate of a substantially rigid material.

6. The shuttle assembly of claim 4, wherein the shuttle bar comprises a plate of a substantially rigid material selected from the group consisting of: an aluminum alloy, a plastic, a composite and a laminate.

7. The shuttle assembly of claim 1, wherein the shuttle pegs are comprised of a chemically inert material.

8. The shuttle assembly of claim 1, wherein the shuttle pegs have an exterior surface comprised of a low friction material.

9. The shuttle assembly of claim 1, wherein the shuttle pegs are comprised of a material selected from the group consisting of a plastic composition, a polytrtrafluoroethylene composition and a molybdenum composition.

10. The shuttle pegs of claim 2, wherein the aspirator tubes are comprised of stainless steel tubing.

11. The shuttle assembly of claim 1, wherein the shuttle bar has at least at least two vertical guide sleeve bores extending through the shuttle bar between the upper and lower bar surfaces.

12. The fluid delivery/removal head of claim 1, wherein the reservoir assembly comprises:
- a manifold block having a substantially flat upper and lower manifold surfaces, and a plurality of fluid reservoirs disposed in a dispenser pattern and extending vertically through the upper and lower manifold surfaces the fluid reservoirs;
- a manifold cover, the manifold cover being substantially flat and adapted to seal against the upper manifold surface and having a plurality of peg guide through apertures disposed in the dispenser pattern, the peg guide apertures each for slideably receiving and fluid sealing against a shuttle peg; and
- a fluid channel between the upper manifold surface and the manifold cover, the fluid channel communicating with each of the fluid reservoirs.

13. The reservoir assembly of claim 12, wherein the manifold cover is removably sealed against the manifold block.

14. The reservoir assembly of claim 12, wherein the manifold cover is fixedly sealed against the manifold block.

15. The reservoir assembly of claim 12, wherein the fluid channel is inset into the upper surface of the manifold block.

16. The reservoir assembly of claim 12, wherein the fluid channel is inset into a lower cover surface of the manifold cover.

17. The reservoir assembly of claim 12, further comprising a manifold gasket disposed between the manifold cover and the manifold block.

18. The reservoir assembly of claim 12, wherein the fluid reservoirs of the manifold block have a cross-section at the upper manifold surface and a depth which the cross-section extends downward from the manifold upper surface toward the manifold lower surface to a peg seat, the peg seat for engaging and sealing an open peg end of a shuttle peg with the center of the peg seat defining a decant passage of the fluid reservoir at the lower manifold block surface.

19. The reservoir assembly of claim 12, wherein the fluid reservoirs of the manifold block have a metered volume for dispensing defined by a volume of the reservoir minus a volume of the shuttle peg when the shuttle peg is seated in the fluid reservoir.

20. The reservoir assembly of claim 12, wherein the fluid reservoirs of the manifold block have a metered volume for dispensing defined by an area of the reservoir cross-section times the reservoir depth minus a volume of the shuttle peg when the shuttle peg is seated in the fluid reservoir.

21. A metered fluid dispenser and aspirating apparatus comprising:
- a combination of a fluid delivery/removal head of claim 1, with the shuttle assembly being variably positionable relative to the fixed reservoir assembly by a head drive mechanism;
- a variably positionable well table for presenting at least one array of sample wells to the combination of the shuttle assembly and the reservoir assembly, the well table positionable by means of a table drive mechanism;
- a fluid handling system comprising fluid source and waste reservoirs in flow communication with the fluid head, for providing controlled delivery and removal of liquid materials between the fluid head and the source and waste reservoirs; and
- a controller assembly, including a central processing unit and appropriate hardware and software, for timed operation and control of the fluid head and head drive, the well table and table drive, and the fluid handling system.

* * * * *